(12) United States Patent
Geric et al.

(10) Patent No.: US 12,667,239 B2
(45) Date of Patent: *Jun. 30, 2026

(54) ENDOSCOPIC VESSEL HARVESTING WITH THERMAL MANAGEMENT AND AUGMENTED REALITY DISPLAY

(71) Applicant: Terumo Cardiovascular Systems Corporation, Ann Arbor, MI (US)

(72) Inventors: Joseph Mark Geric, Livonia, MI (US); Takeshi Tsubouchi, Dexter, MI (US); Randal James Kadykowski, South Lyon, MI (US); Tatsunori Fujii, Bear, DE (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,372

(22) Filed: Mar. 12, 2024

(65) Prior Publication Data

US 2024/0206704 A1     Jun. 27, 2024

Related U.S. Application Data

(63) Continuation of application No. 17/399,229, filed on Aug. 11, 2021, now Pat. No. 12,053,150.

(51) Int. Cl.
*A61B 1/00* (2006.01)
*A61B 1/04* (2006.01)
(Continued)

(52) U.S. Cl.
CPC ...... *A61B 1/0005* (2013.01); *A61B 1/000095* (2022.02); *A61B 1/044* (2022.02);
(Continued)

(58) Field of Classification Search
CPC . A61B 1/0005; A61B 1/000095; A61B 1/044; A61B 5/0035; A61B 5/015;
(Continued)

(56) References Cited

U.S. PATENT DOCUMENTS 4,878,113 A     10/1989   Nakamura
5,233,515 A      8/1993   Cosman
(Continued)

FOREIGN PATENT DOCUMENTS

DE     10-2009049399 A1     2/2011
EP           2997926        4/2019
(Continued)

OTHER PUBLICATIONS

Extended European Search Report in European Appln. No. 22188615. 3, mailed on Jan. 9, 2023, 6 pages.
Maquet, "Envision the Future of EVH," brochure, 2009, 2 pages.

*Primary Examiner* — Anh Tuan T Nguyen
*Assistant Examiner* — Shankar Raj Ghimire
(74) *Attorney, Agent, or Firm* — Fish & Richardson P.C.

(57)     ABSTRACT

A vessel harvesting system removes a target vessel from a patient for use as a bypass. An elongated harvesting instrument inserts into a body along a path of a target vessel which includes at least one side branch. The harvesting instrument includes a cutter for applying thermal energy to sever and cauterize the side branch. An endoscopic camera captures visible-light images from a distal tip of the instrument within a dissected tunnel around the target vessel. A thermal camera captures thermograms coinciding with the visible-light images to characterize a temperature present at respective surfaces in the tunnel. An image processor (e.g., an electronic controller) renders a video stream including the visible-light images and an overlay depicting the temperatures present on at least some of the respective surfaces when applying the thermal energy. A display presenting the (Continued)

video stream and overlay to a user can be an augmented-reality display.

20 Claims, 10 Drawing Sheets

(51) Int. Cl.

| | |
|---|---|
| *A61B 5/00* | (2006.01) |
| *A61B 5/01* | (2006.01) |
| *A61B 18/00* | (2006.01) |
| *A61B 90/00* | (2016.01) |
| *A61B 17/00* | (2006.01) |
| *A61B 18/14* | (2006.01) |

(52) U.S. Cl.
CPC ............ *A61B 5/0035* (2013.01); *A61B 5/015* (2013.01); *A61B 1/00048* (2013.01); *A61B 2017/00119* (2013.01); *A61B 2017/00969* (2013.01); *A61B 2018/00428* (2013.01); *A61B 2018/00595* (2013.01); *A61B 2018/00601* (2013.01); *A61B 2018/00904* (2013.01); *A61B 2018/00982* (2013.01); *A61B 18/1445* (2013.01); *A61B 2090/365* (2016.02)

(58) Field of Classification Search
CPC ............ A61B 1/00048; A61B 18/1445; A61B 2018/00428; A61B 2018/00595; A61B 2018/00601; A61B 2018/00904; A61B 2090/365; A61B 2017/00084; A61B 90/361; A61B 1/046; A61B 2018/00404; A61B 17/00008
See application file for complete search history.

(56) References Cited

U.S. PATENT DOCUMENTS

| | | | |
|---|---|---|---|
| 6,694,181 | B2 | 2/2004 | Kokate |
| 7,331,971 | B2 | 2/2008 | Kasahara et al. |
| 7,547,314 | B2 | 6/2009 | Kadykowski |
| 8,048,100 | B2 | 11/2011 | Kadykowski et al. |
| 8,702,700 | B2 | 4/2014 | Maeda et al. |
| 9,360,934 | B2 | 6/2016 | Ruiz Morales et al. |
| 9,474,580 | B2 | 10/2016 | Hannaford et al. |
| 9,646,423 | B1 | 5/2017 | Sun et al. |
| 9,861,446 | B2 | 1/2018 | Lang |
| 9,980,780 | B2 | 5/2018 | Lang |
| 10,092,355 | B1 | 10/2018 | Hannaford et al. |
| 10,152,789 | B2 | 12/2018 | Carnes et al. |
| 10,426,345 | B2 | 10/2019 | Shekhar et al. |
| 10,624,663 | B1 | 4/2020 | Barral et al. |
| 10,978,284 | B2 | 4/2021 | Pringle |
| 2003/0187319 | A1* | 10/2003 | Kaneko .................... A61N 2/00 600/9 |
| 2006/0195014 | A1 | 8/2006 | Seibel |
| 2009/0024023 | A1 | 1/2009 | Welches et al. |
| 2009/0043223 | A1 | 2/2009 | Zhang et al. |
| 2009/0137893 | A1 | 5/2009 | Seibel et al. |
| 2010/0292533 | A1 | 11/2010 | Kasahara et al. |
| 2011/0245735 | A1 | 10/2011 | Eckhouse |
| 2011/0306986 | A1 | 12/2011 | Lee et al. |
| 2012/0035606 | A1 | 2/2012 | Kano et al. |
| 2013/0041292 | A1 | 2/2013 | Cunningham |
| 2014/0236020 | A1 | 8/2014 | Leschinsky |
| 2015/0141808 | A1 | 5/2015 | Elhawary et al. |
| 2016/0073876 | A1 | 3/2016 | Akita et al. |
| 2016/0157880 | A1 | 6/2016 | Aklog |
| 2016/0262602 | A1 | 9/2016 | Yu |
| 2017/0027645 | A1 | 2/2017 | Ben Oren et al. |
| 2017/0367771 | A1 | 12/2017 | Tako et al. |
| 2018/0047555 | A1 | 2/2018 | Pringle et al. |
| 2018/0168734 | A1 | 6/2018 | Strobl |
| 2018/0271603 | A1 | 9/2018 | Nir et al. |
| 2018/0310811 | A1 | 11/2018 | Meglan et al. |
| 2019/0339850 | A1* | 11/2019 | Ho ........................ A61B 5/0066 |
| 2020/0008866 | A1* | 1/2020 | Fujii .................. A61B 18/1482 |
| 2020/0226758 | A1* | 7/2020 | Carnes .................. H04N 23/60 |
| 2021/0077195 | A1 | 3/2021 | Saeidi et al. |
| 2021/0177531 | A1 | 6/2021 | Lennartz |
| 2021/0196384 | A1 | 7/2021 | Shelton, IV et al. |
| 2021/0196425 | A1 | 7/2021 | Shelton, IV et al. |
| 2021/0397865 | A1 | 12/2021 | Juergens |
| 2022/0280224 | A1 | 9/2022 | Kabaya |
| 2023/0101750 | A1 | 3/2023 | Shelton, IV et al. |
| 2023/0103005 | A1 | 3/2023 | Shelton, IV et al. |

FOREIGN PATENT DOCUMENTS

| | | | |
|---|---|---|---|
| JP | 2006149846 A | 6/2006 | |
| JP | 2007136133 A | 6/2007 | |
| JP | 2010507404 A | 3/2010 | |
| JP | 2013540517 A | 11/2013 | |
| JP | 2015529477 A | 10/2015 | |
| WO | WO-2019239410 A1 * | 12/2019 | ........... A61B 5/0088 |

* cited by examiner

Image Data

ENDOSCOPIC VESSEL HARVESTING WITH THERMAL MANAGEMENT AND AUGMENTED REALITY DISPLAY

CROSS-REFERENCE TO RELATED APPLICATION

This application is a continuation of U.S. application Ser. No. 17/399,229, filed on Aug. 11, 2021, the contents of which are incorporated by reference in its entirety.

TECHNICAL FIELD

The present disclosure relates to vessel harvesting, and more particularly, to endoscopic vessel harvesting.

BACKGROUND

The present disclosure relates in general to devices and methods for endoscopic harvesting of a blood vessel within the limb of a patient using applied thermal energy to cut and cauterize tissues and side branches, and, more specifically, to providing thermal management within an endoscopic vessel harvesting system which may include an augmented-reality device worn by a person performing the harvesting procedure.

In connection with coronary artery bypass grafting (CABG), a blood vessel or vessel section, such as an artery or vein, is "harvested" (i.e., removed) from its natural location in a patient's body to use it elsewhere in the body. In CABG surgery, for example, the blood vessel is used to form a bypass between an arterial blood source and the coronary artery that is to be bypassed. Among the preferred sources for the vessel to be used as the bypass graft are the saphenous veins in the legs and the radial arteries in the arms.

Endoscopic surgical procedures for subcutaneously harvesting a section of a vein (e.g., the saphenous vein) have been developed in order to avoid disadvantages and potential complications of harvesting through a continuous incision. One such minimally-invasive technique employs a small incision for locating the desired vessel and for introducing one or more endoscopic harvesting devices. Primary dissection occurs by introduction of a dissecting instrument through the incision to create a working space and separate the vessel from the surrounding tissue. Then a cutting instrument is introduced into the working space to sever the blood vessel from the connective tissue and side branches of the blood vessel. The branches may be cut and cauterized using the cutting instrument.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph Plus® Endoscopic Vessel Harvesting System from Terumo Cardiovascular Systems Corporation of Ann Arbor, Michigan. An endoscopic vessel harvesting system of this type is also shown in U.S. Pat. Nos. 7,331,971 and 8,048,100 and U.S. patent application publications 2010/0292533 and 2012/0035606, which are incorporated herein by reference in their entirety.

The dissector tool typically comprises a longitudinal stainless steel or plastic rod with a tip at one end and an operator handle at the other. The rod may have a coating of PTFE to reduce sliding resistance. The tip is tapered to a blunt end and is made of transparent plastic. The dissection proceeds along the perimeter of the vessel being harvested to separate it from the surrounding tissue and to expose the side branches of the vessel so that they can be severed with the cutting tool. In the VirtuoSaph® Plus System, the cutting tool for severing and cauterizing branches has the form of a V-cutter wherein a V-shaped tip is extendable from the distal end of the unit to guide a branch to be cut into a longitudinal slit. Electrodes adjacent the slit are electrically energized with a high frequency voltage in order to cauterize and sever the branch by coagulation (e.g., bipolar electrosurgical energy). A V-keeper also extends from the distal end in order to capture the vessel and to guide the tool along the vessel.

An internal endoscopic view is provided to the user via an optical system having a camera and a video display. The camera can be mounted within the distal tip of the harvesting device. Alternatively, a lens and optical fiber installed in the harvesting device can carry an image to a camera located at a remote end of the optical fiber outside the harvesting device or in the handle of the device. The field of view is illuminated by a light source such as an LED mounted at the tip of the harvesting device (dissector or cutter) or a remote source which inputs light to an optical fiber which runs through the harvesting device to emit light from the tip.

The endoscopic camera view during the dissection or cutting phases is displayed on a computer monitor. Significant training may be required for a user to become skilled in properly coordinating their movements with the dissecting/cutting instruments while looking away from the patient toward the monitor.

Thermal energy applied to side branches or to connective tissues around the target vessel has a potential to spread to the target vessel, especially if a side branch is severed at a point that is too close to the target vessel. Heat damage to a target vessel may accumulate during a harvesting procedure which can occur undetected until the target vessel is finally removed from the body and inspected.

SUMMARY

In one aspect of the disclosure, a vessel harvesting system comprises an elongated harvesting instrument for insertion into a body along a path of a target vessel, wherein the target vessel connects to at least one side branch, and wherein the harvesting instrument includes a cutter for applying thermal energy to sever and cauterize the side branch. An endoscopic camera is mounted to the harvesting instrument to capture visible-light images from a distal tip of the instrument within a dissected tunnel around the target vessel. A thermal camera is mounted to the harvesting instrument to capture thermograms (i.e., thermal images) coinciding with the visible-light images to characterize a temperature present at respective surfaces in the tunnel. An image processor (e.g., controller) renders a video stream including the visible-light images and an overlay depicting the temperatures present on at least some of the respective surfaces when applying the thermal energy. A display presents the video stream and overlay to a user. The display can be a computer monitor or an augmented-reality display, for example.

DETAILED DESCRIPTION

The present disclosure is related to co-filed application U.S. serial no. (0320PRO), entitled Augmented-Reality Endoscopic Vessel Harvesting, which is incorporated herein by reference in its entirety.

Figure 1:
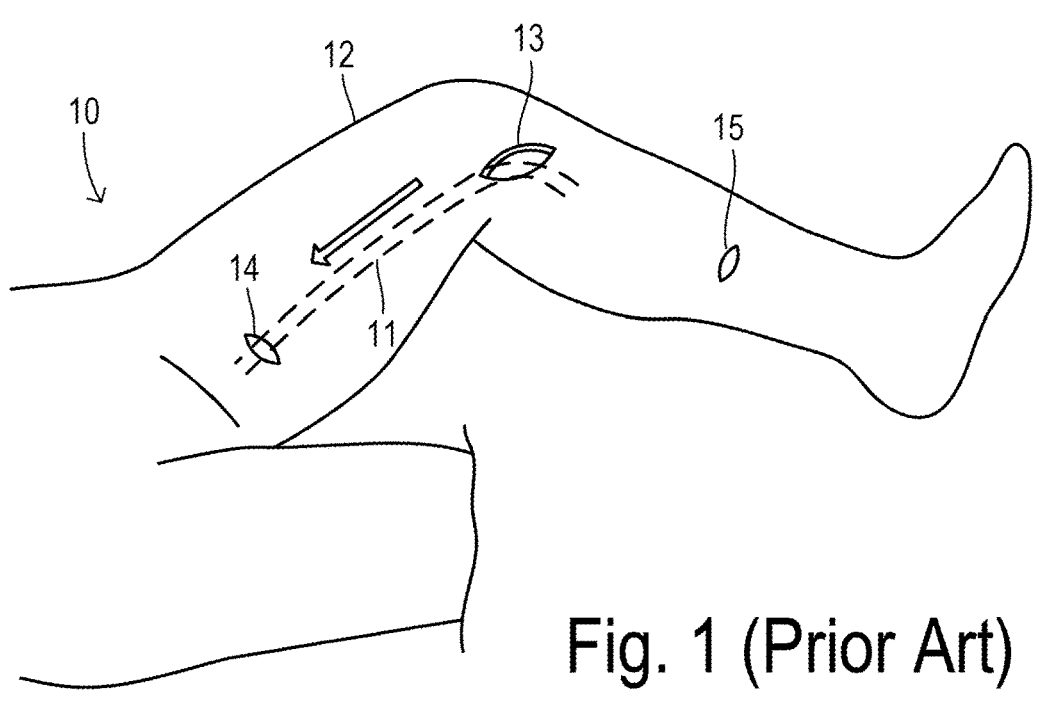
FIG. 1 is an external view of a saphenous vein being harvested from a leg.

Referring to FIG. 1, a patient 10 has a saphenous vein 11 within a lower limb 12. An incision 13 is made directly above vein 11, and tissue is peeled back from incision 13 to access the vein. Endoscopic instruments are inserted through incision 13 to separate vein 11 from connective tissue and then to sever and cauterize side branches that extend from vein 11. A second incision or stab wound 14 is created at a second position on limb 12 so that a second end of vein 11 can be severed. Vein 11 is then extracted through one of the incisions. The entry point and/or second incision or stab wound can be placed at various locations along vein 11 as shown at 15.

Figure 2:
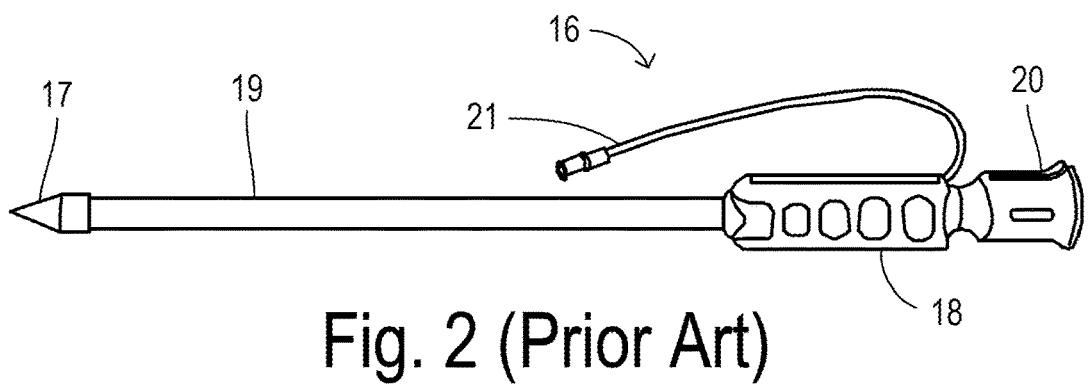
FIG. 2 is a side view of a prior art dissector unit.

A known dissector unit 16 is shown in FIG. 2 for endoscopic dissection of a saphenous vein or other vessel by insertion through an initial incision and then pressing a dissector tip 17 into the fat along the direction of the vessel to separate it from adjacent tissue. Dissector unit 16 has a handle 18 connected to a longitudinal rod 19 having dissector tip 17 at its distal end. A receiver 20 at the end of handle 18 receives an endoscope and optical cable (not shown) for extending through rod 19 to dissector tip 17 which is transparent in order to allow visualization of the vessel and surrounding tissue. An insufflation tube 21 passes through handle 18 and is part of an insufflation gas channel extending to a release hole in or near tip 17. Tube 21 is connected to a source of $CO_2$ or other insufflation gas for filling the cavity adjacent the vessel as it is being formed.

Figure 3:
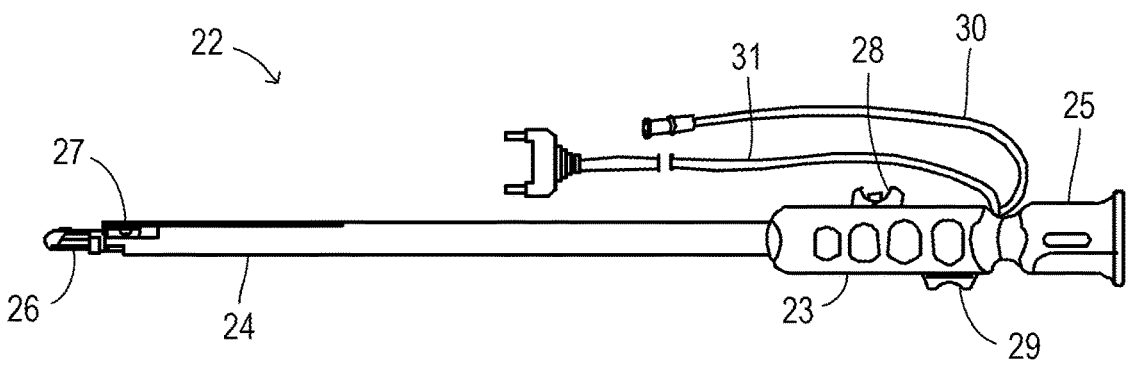
FIG. 3 is a side view of a prior art cutting unit.

After initial blunt dissection around the vessel, a harvester cutting unit 22 as shown in FIG. 3 is used subcutaneously to grasp the vessel being dissected and to sever any branches or connective tissue connecting to the vessel. Harvester 22 has a handle 23 connected to an elongated sleeve member 24 and an endoscope receiver 25. At the distal end of sleeve 24 are a vessel keeper (V-keeper) 26 for retaining the vessel being dissected and a vessel cutter (V-cutter) 27 for severing branches. V-keeper 26 is manipulated by V-keeper buttons 28 on handle 23. V-cutter 27 is extended or retracted by manipulating a V-cutter extender button 29 on handle 23. An insufflator tube 30 is adapted to be connected to an insufflation source to deliver the gas to the distal end of sleeve 24 via a gas channel extending between handle 23 at the proximal end and a release hole at the distal end. A bipolar or integrated bipolar cord 31 connects to a source of high frequency voltage, and includes conductors for supplying the voltage to electrodes on V-cutter 27 for cutting and cauterizing the side branches and connective tissue.

In some embodiments, cutting and cauterizing may be accomplished using a pair of scissor-like jaws instead of a V-cutter. The jaws may have electrodes or other energizable devices on inner surfaces that are clamped onto a side branch for being cut.

Figure 4:
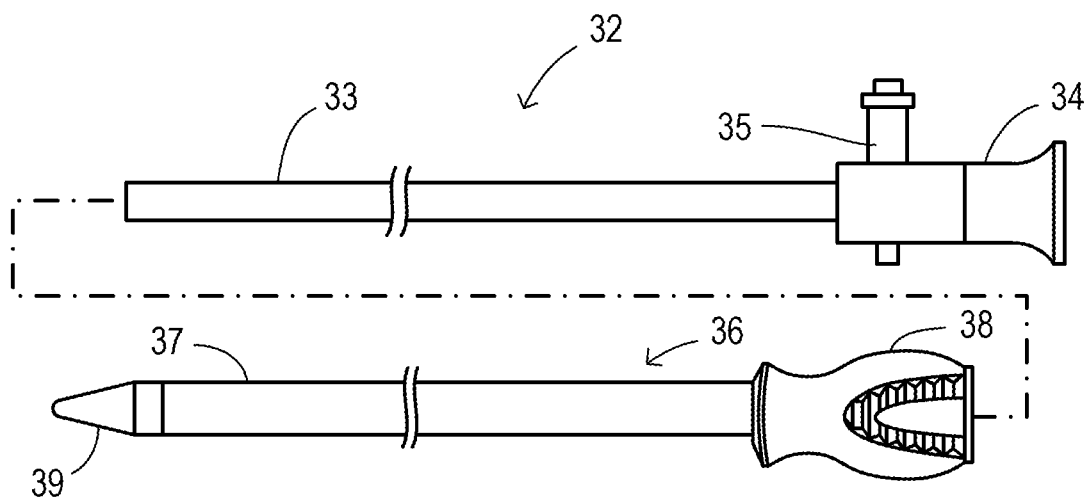
FIG. 4 is a plan view of another prior art blunt dissector with an endoscope.
Figure 5:
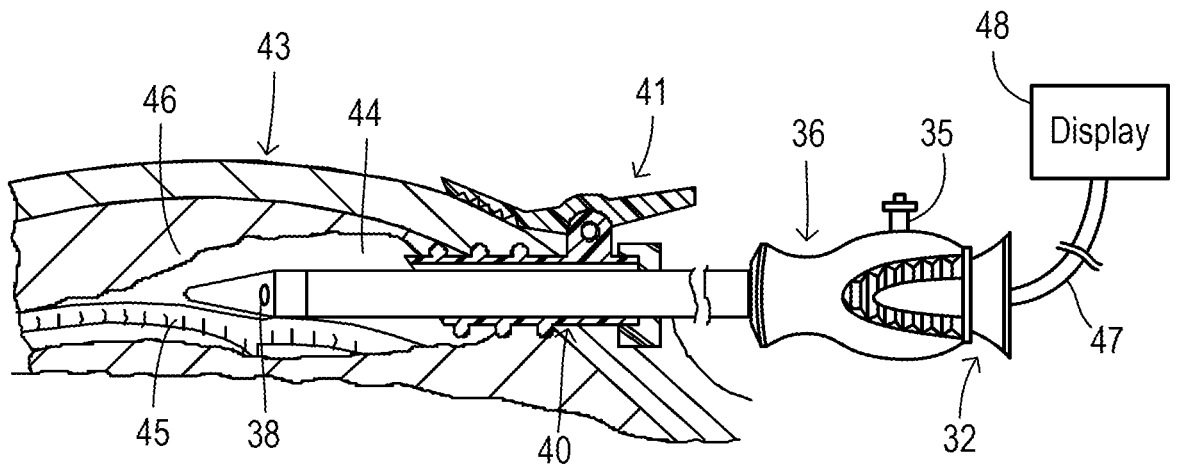
FIG. 5 is a partial cross-sectional view of the dissection of a blood vessel.

FIGS. 4 and 5 show another vessel harvesting system which includes an endoscope unit 32 to perform observation in a patient's body, a dissector unit 36 to dissect a blood vessel in the body, and a trocar 40 to help insert the endoscope 32 and dissector unit 36 into the body. An optical system is shown as a rigid endoscope 32 which has an elongated rod-like inserting portion 33. The proximal end of inserting portion 33 connects to an end adapter 34 to transmit an endoscopic image. A light guide port 35 projects from end adapter 34 to connect to a light guide cable which supplies illumination light to endoscope 32. In other embodiments, the optical system can employ a camera and LED light source installed at the distal end of endoscope 32 connected via electrical cables to power and a video image processor.

Dissector unit 36 has a tubular main body portion comprising a hollow longitudinal rod 37 within which endoscope 32 is to be inserted. Endoscope 32 is inserted or removed from longitudinal rod 37 through a handle portion 38. The material of longitudinal rod 37 may be comprised of fluoropolymers. The most preferred material for constituting the outer surface of longitudinal rod 37 is polytetrafluoroethylene (PTFE). The use of a fluoropolymer reduces the friction caused by moving rod 37 through connective tissue, thereby reducing the force required to perform a dissection.

A blunt dissector tip 39 is disposed at the distal end of longitudinal rod 37. Tip 39 has a conical shape and comprises a transparent synthetic resin material to facilitate viewing through tip 39 using endoscope 32. Trocar 40 guides dissector unit 36 into the incision site. An outer surface of trocar 40 includes a projection to engage with living tissue and a holding portion 41 to hold trocar 40 onto the living tissue 43 (e.g., patient's skin). Since the inserting direction of dissector 36 is along the direction of a target blood vessel 45 being dissected, the operator gradually inserts the dissector so as to dissect peripheral tissue 46 from blood vessel 45 (creating a working tunnel 44) while viewing the endoscope image on a display 48 which is connected to endoscope 32 by cables 47.

Figure 6:
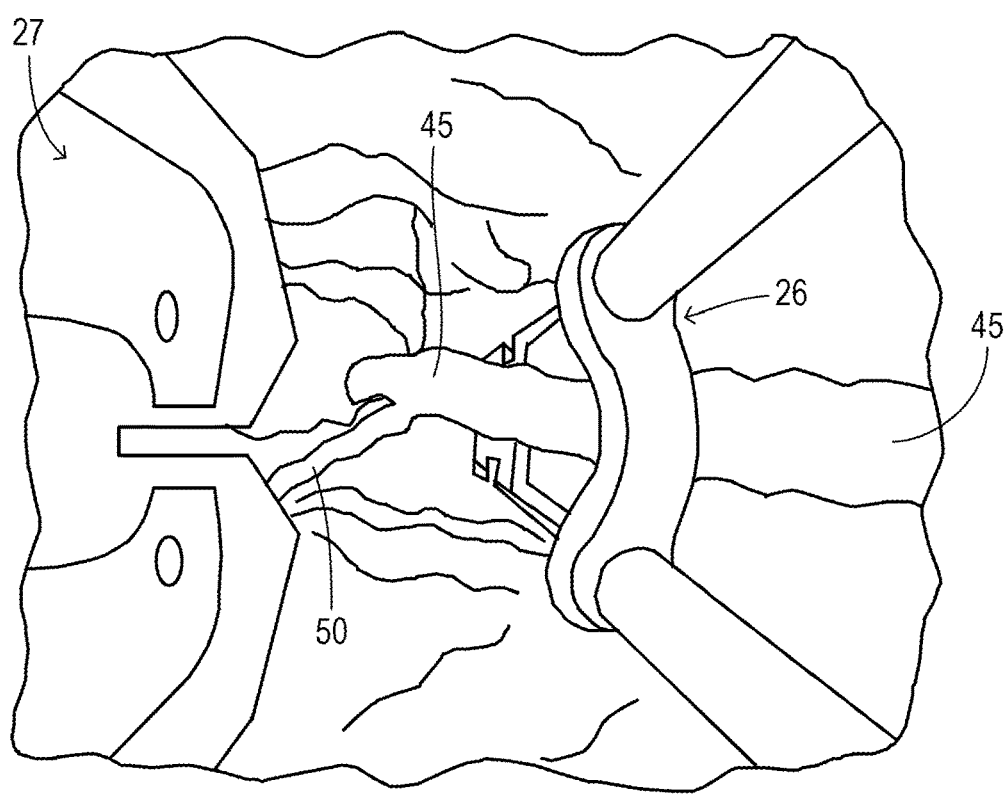
FIG. 6 is an endoscopic camera view depicting a V-keeper and a V-cutter of the harvester unit deployed within a working tunnel around a target vessel.

After dissecting a working tunnel along the target vessel, a dissector instrument may be removed and a cutting instrument may be inserted into the working tunnel to sever the target vessel from any side branches and from any connective tissue that has not been dissected. FIG. 6 shows an endoscopic view as seen during vessel harvesting wherein a target vessel 45 (e.g., saphenous vein) is retained within V-keeper 26. A side branch 50 extends from vessel 45 within the tunnel created previously during blunt dissection. V-cutter 27 is in position for extending toward side branch 50 for cauterizing and severing it to prepare a section of vessel 45 for removal. Since side branches such as side branch 50 extend in various radial directions away from vessel 45, the harvester must be rotated around vessel 45 to directly approach all the different side branches along the length of vessel 45 being harvested.

Figure 7:
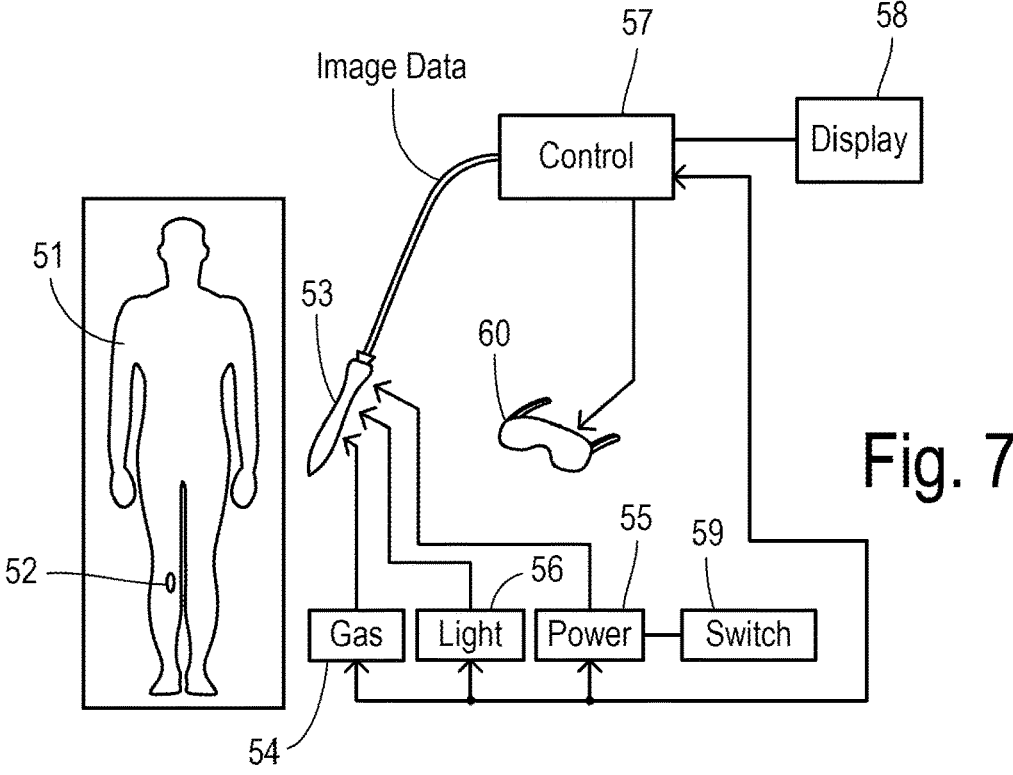
FIG. 7 is a block diagram showing one embodiment of a vessel harvesting system with augmented reality.

FIG. 7 shows a first embodiment of a vessel harvesting system which uses augmented reality. A patient 51 has an incision 52 where a harvesting instrument (e.g., dissector or cutter) 53 is inserted. Instrument 53 is coupled to a source of insufflation gas 54, a power source 55, and a light source 56. Camera images from instrument 53 are coupled to a controller (e.g., image processor) 57, and processed images may be coupled to a conventional display 58 (such as a computer monitor) and/or an augmented-reality display 60.

Power 55 may be provided to instrument 53 under control of a switch 59 (e.g., a foot pedal switch) when a cutter of a cutting instrument has been positioned to cut/cauterized a side branch or connective tissue, or to spot cauterize a tunnel wall, for example. Other control selectors such as a switch on a handle of instrument 53 could also be utilized by a user to energize cutting electrodes on a cutter at the desired moment. A magnitude of energy applied by the cutter for cutting and cauterizing may be controlled by a duration for which switch 59 is activated, or by controlling a magnitude of an applied voltage, or by varying a modulation pattern of an applied voltage, for example.

Augmented reality (AR) is an interactive experience of a real-world environment where the objects that reside in the real world are enhanced by computer-generated perceptual information, sometimes across multiple sensory modalities, including visual, auditory, haptic, somatosensory, and olfactory. In particular, an augmented-reality display may include eyewear with an open viewfield for viewing physical objects and an augmented viewing portion configured to render glyphs and/or video content (e.g., streaming video images).

Augmented-reality display 60 may be comprised of a head-worn display, sometimes also referred to as "smart glass" or "smart glasses", among other names. For example, display 60 can take the form of a pair of glasses, a visor, an open area, or a face-shield that a user (e.g., a surgical technician or physician's assistant) wears on their head or face during a harvesting procedure. Display 60 includes a viewfield through which a user can view physical objects in their field of view, which is sometimes referred to as "non-occluded" or "non-occluded heads-up display (HUD)", among other names. For example, there may be a clear portion of glass, plastic, or similar transparent material through which light emitted from physical objects passes into the user's eye. In some embodiments, display 60 may include solid or opaque portions that completely or partially occludes the user's view, sometimes referred to as "occluded" or an "occluded HUD", among other names. The viewfield can include one or more screens (e.g., Light Emitting Diode or LED screens) along with one or more cameras that capture a video data from the user's point-of-view. Video is then rendered on the screens, providing the user with a viewfield that is similar to a clear view of the physical environment.

In another example, display 60 can include a retinal projector configured to project an image directly onto the wearer's eye or eyes. In some cases, the retinal projector can include a clear portion of glass, plastic, or similar transparent material through which light emitted from physical objects passes into the user's eye. In some cases, a display 60 with retinal projector can include one or more cameras that capture a video data of the user's point-of-view. Video is then rendered and projected onto the user's eye, or eyes, providing the user with a viewfield that is similar to a clear view of the physical environment. In some implementations, display 60 can be configured to account for seeing difficulties of the user. For example, a retinal projector can be configured to provide a projection to a user with a cloudy cornea or cataracts in a way that is clear to such a user.

In yet another example, display 60 can include a half-mirrored portion of glass, plastic, or similar transparent material through which light emitted from physical objects passes into the user's eye, while light is emitted onto the half-mirror view field to render glyphs, etc.

Augmented-reality display 60 is configured to render glyphs (e.g., text, symbols, colored overlays, etc.) and to render video in the viewfield. For example, light emitters can emit light into a transparent viewfield so that the user is shown a reflection of the light. In another example, where screens are used to show video from the user's point-of-view, the glyphs and video can be shown superimposed over the point-of-view video. In any case, display 60 shows a presentation of the glyphs and the video as an overlay superimposed on the view of the physical objects.

Display 60 can include other features as well. For example, a microphone and earphone may be included for connecting to an intercom, cellular phone, or other telecommunication device. This can allow the operator to communicate, via the microphone and earphone, with people in the same facility or more distant.

As discussed in more detail below, many different types of glyphs and video images can be displayed to the user. A selector (not shown) may enable the user to generate a screen update command in order to modify the contents of display 60 (e.g., selecting different glyphs, scrolling through monitored physiologic parameters of the patient, selecting different image sources, or altering characteristics of the displayed items such as zooming in on a region of the images). Since it is desirable for the user (e.g., wearer of display 60) to maintain their hand grip on the harvesting instrument, a selector may be configured to receive commands while the user continues to hold the instrument. A selector may be comprised of a manual control (e.g., an electrical pushbutton switch or toggle) mounted on the instrument in its gripping area. Otherwise, a selector may be comprised of a hands-free device which senses other actions by the user. For example, the selector may include an eye-tracking camera which detects specified eye movements of the user which have been designated to trigger a corresponding update command. Alternatively, the selector may include either 1) a microphone and a voice recognition system so that the user can generate the screen update command as a spoken command, 2) a motion sensor responsive to predetermined movements of the user, or 3) a foot pedal (e.g., coupled to image processor 57 via a Bluetooth® connection) with one or more switches to generate a desired update command.

Figure 8:
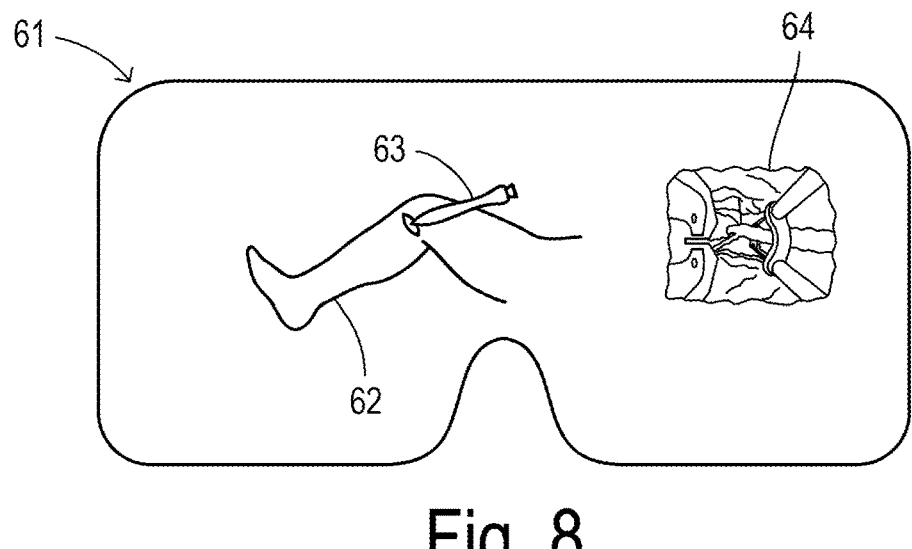
FIG. 8 is a schematic diagram showing an augmented-reality presentation which includes a streaming endoscopic video image overlaid on a real view.

FIG. 8 shows an example of a viewfield 61 on and through an augmented-reality display as seen by a user (e.g., wearer of a head-mounted display). A transparent portion of viewfield 61 without overlays provides a real, live view of the scene around the wearer which includes a patient's limb 62 and an endoscopic instrument 63. An overlay 64 provides a copy of the instantaneous endoscopic image being received by the image processor/controller from the endoscopic camera (e.g., displayed toward a lateral side of the viewfield).

Figure 9:
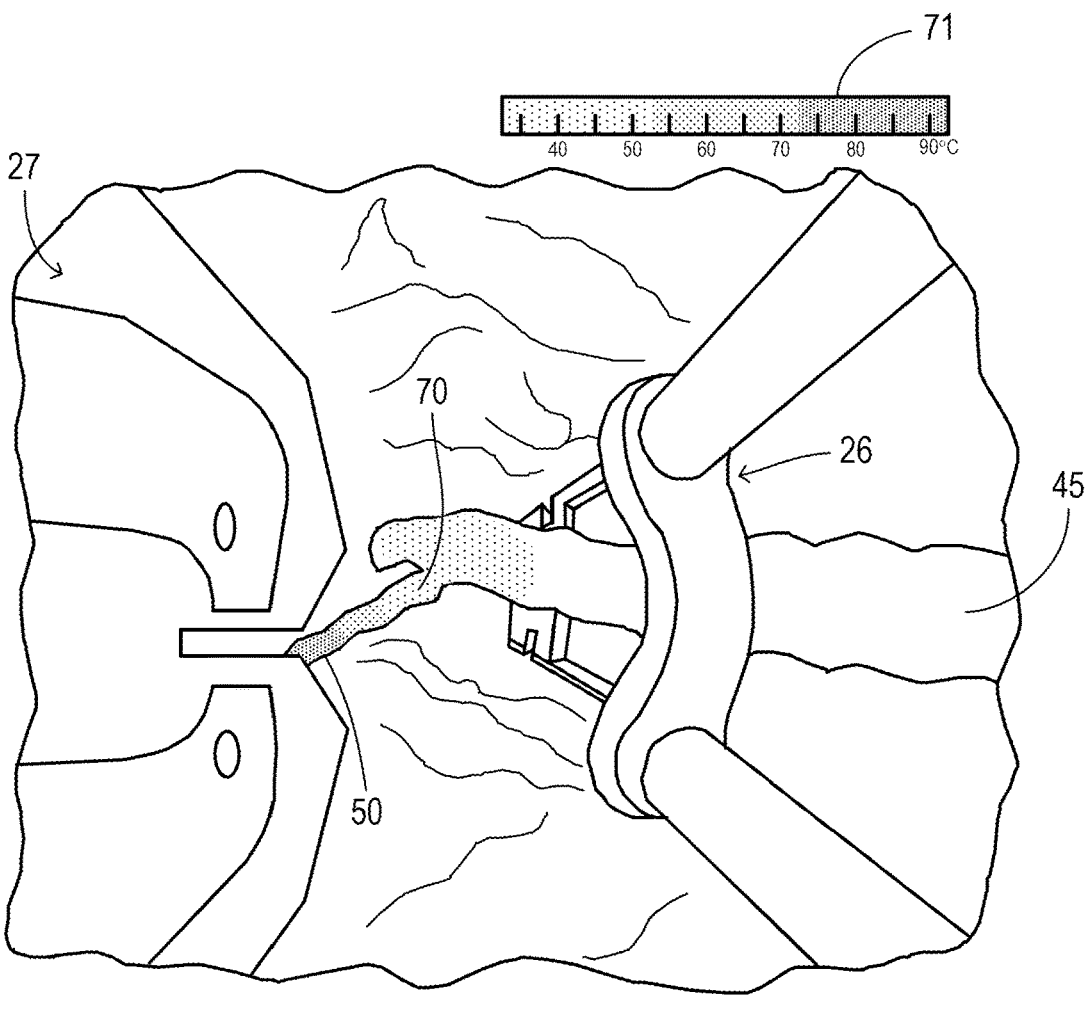
FIG. 9 shows an endoscopic visible-light view with an overlay depicting temperatures of selected surfaces obtained using a thermal imager.

In addition to visible-light endoscopic images for guiding and using the harvesting instruments, the present disclosure employs a thermal camera coupled with the harvesting instrument (e.g., carried along with the endoscope) so that the image data includes a temperature overlay based on thermograms captured by the thermal camera. The overlay of temperature data enables the user to monitor the heating of the target vessel and side branches and to better manage the overall heat load experienced by different regions of the target vessel for maintaining the health of the target vessel. FIG. 9 shows an example display view (e.g., as seen on a computer monitor) combining an endoscopic visible-light image (including V-keeper 26, V-cutter 27, target vessel 45, and side branch 50) with a color-tinted temperature overlay 70. Temperature overlay 70 may encode lower temperatures with cooler colors (e.g., from blue to green with rising temperature) and higher temperatures with warmer colors (e.g., from yellow to red with rising temperature). A color key 71 can be displayed as part of the overlay in order to show a visual correspondence between color and temperature. As an alternative to color tinting, a temperature overlay can be generated as regions of speckles or dots of corresponding colors. Preferably, the temperature overlay may be limited to relevant surfaces within the visible-light view such as the side branches, target vessel, and tunnel wall. Restriction of temperature overlay 70 to just the significant locations can be obtained by 1) using pattern recognition of the visible-light images to localize side branch 50 and the nearby portions of target vessel 45, or 2) by only representing temperatures over a predetermined threshold (e.g., 40° C.) which lies between a normal body temperature and a temperature which would only be present in response to use of the cutting/cauterizing electrodes, for example.

Figure 10:
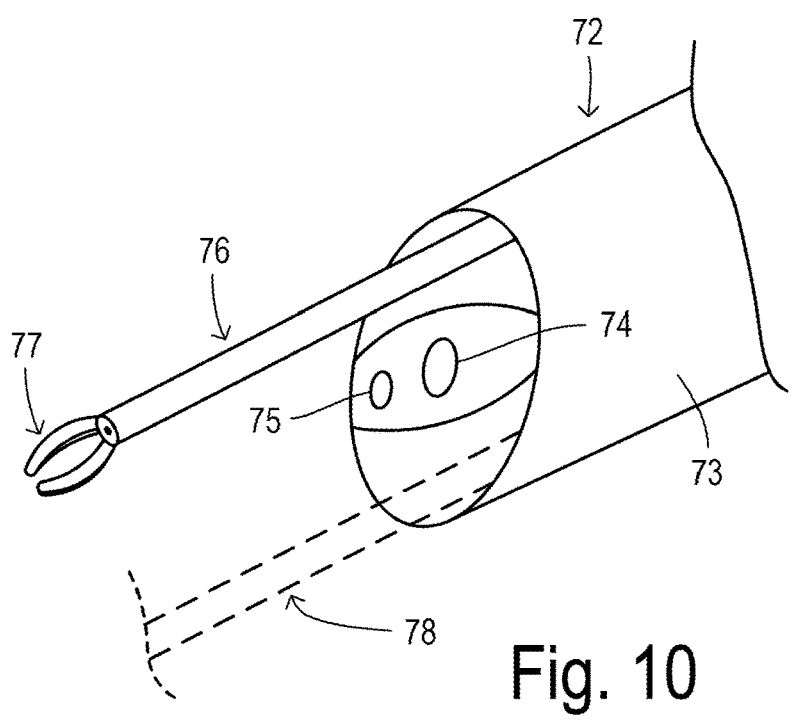
FIG. 10 is a perspective view of a display end of a harvesting instrument with cutting jaws and having visible-light and thermal cameras.

FIG. 10 shows a harvesting instrument in the form of a cutting tool 72 having an elongated body 73. At a distal end of body 73, there are a visible light imager 74 and a thermal imager 75. A cutter 76 may be slidable longitudinally within body 73 and may have articulating joints in order to place a pair of jaws 77 into position over a side branch to be cut/cauterized. Jaws 77 may include bipolar electrodes on their inward facing surfaces to apply heat to a side branch compressed between jaws 77. Tool 72 may further include a V-keeper 78.

Visible light imager 74 may comprise a rigid rod (e.g., glass or optical fiber) with a shaped distal end or carrying a lens for providing an endoscopic view. A proximal end (not shown) of the rigid rod may have an eyepiece and/or an optical connection to a camera for capturing images which are transmitted to an image processor. Light from a light port (not shown) may be emitted from the distal end of the rod for illuminating the tunnel with visible light. Alternatively, imager 74 may comprise an electronic image sensor (e.g., CCD camera) and an LED for illuminating the tunnel. Imager 74 could also be comprised of a stereoscopic viewer (either an electronic 3D imager or a rigid 3D endoscope) to obtain depth information that can assist in identifying the target vessel and/or side branches.

Thermal imager 75 may comprise a passive, thermo-sensitive array which is arranged to detect surface temperatures as a thermograph overlapping with the visible-light image. A pixel size (e.g., resolution) in the thermograph does not need to be as fine as the visible-light pixels. The resolution would only need to be sufficient to depict rough temperature gradients as needed to identify regions receiving excessive heating.

Figure 11:
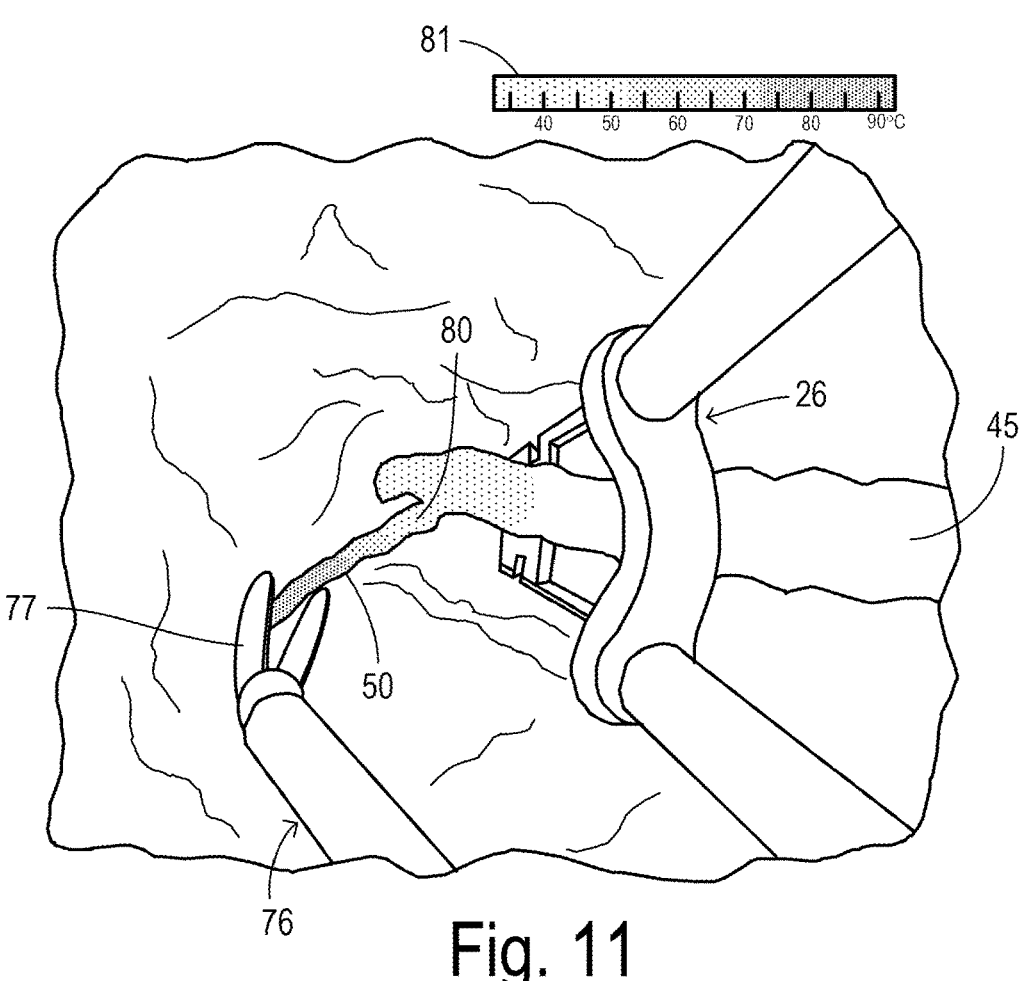
FIG. 11 shows another endoscopic visible-light view with an overlay depicting temperatures of selected surfaces obtained using a thermal imager.

FIG. 11 shows another displayed video frame with a temperature overlay wherein cutter 76 with jaws 77 is being used to sever side branch 50. For clarity, jaws 77 are shown open at a position nearby a cutting area of side branch 50 while a temperature overlay 80 and color key 81 correspond to temperature data that would be seen with jaws being compressed onto side branch 50 with the electrodes being activated (e.g., with a maximum temperature being generated in side branch 50 at the point of contact and with elevated temperatures spreading through side branch 50 and onto target vessel 45). By depicting the temperature data, a user is provided with an awareness of the heating that has resulted from their cutting/cauterizing actions, and they can respond accordingly.

Figure 12:
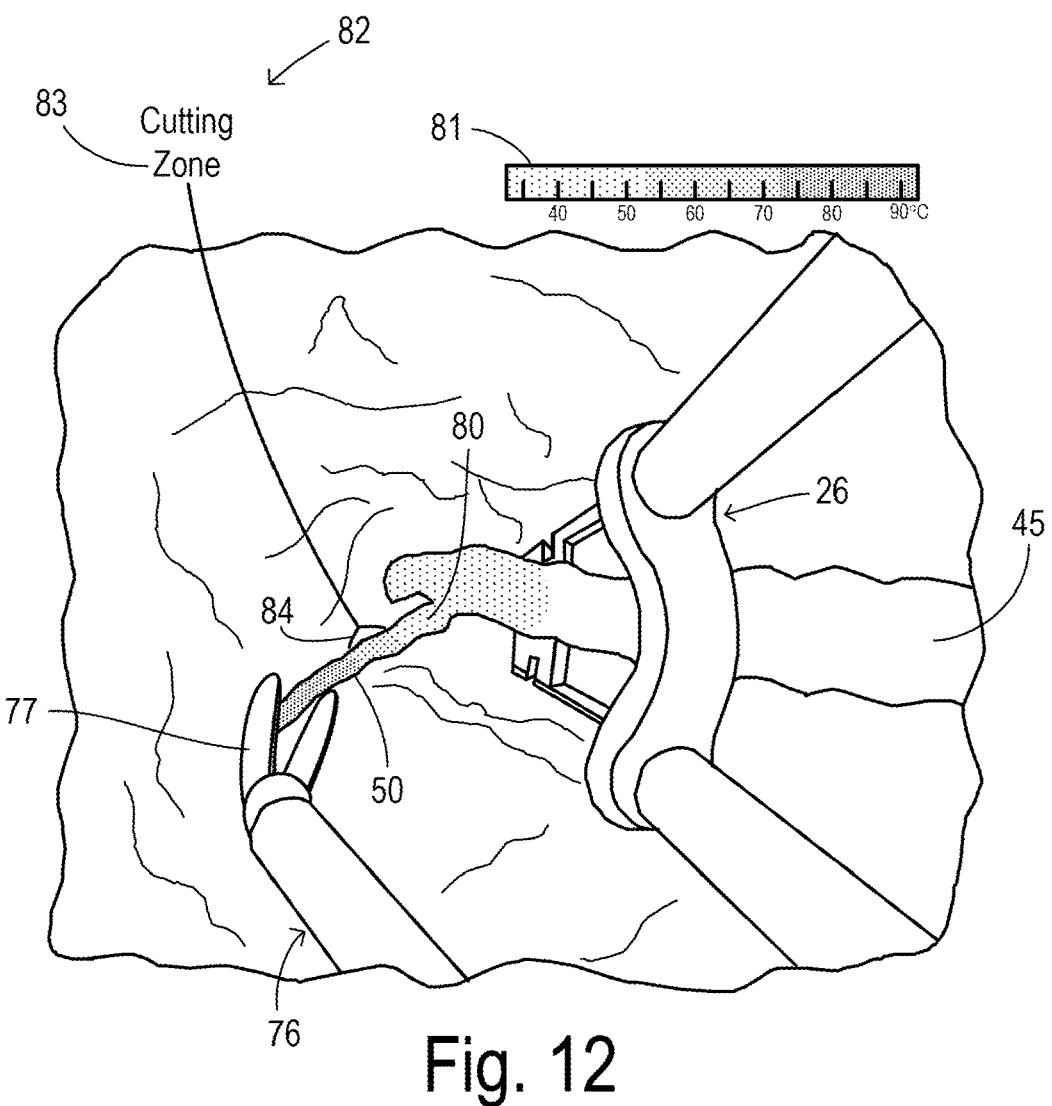
FIG. 12 shows an endoscopic visible-light view with an additional overlay pointing to an optimal location for cutting a side branch.
Figure 13:
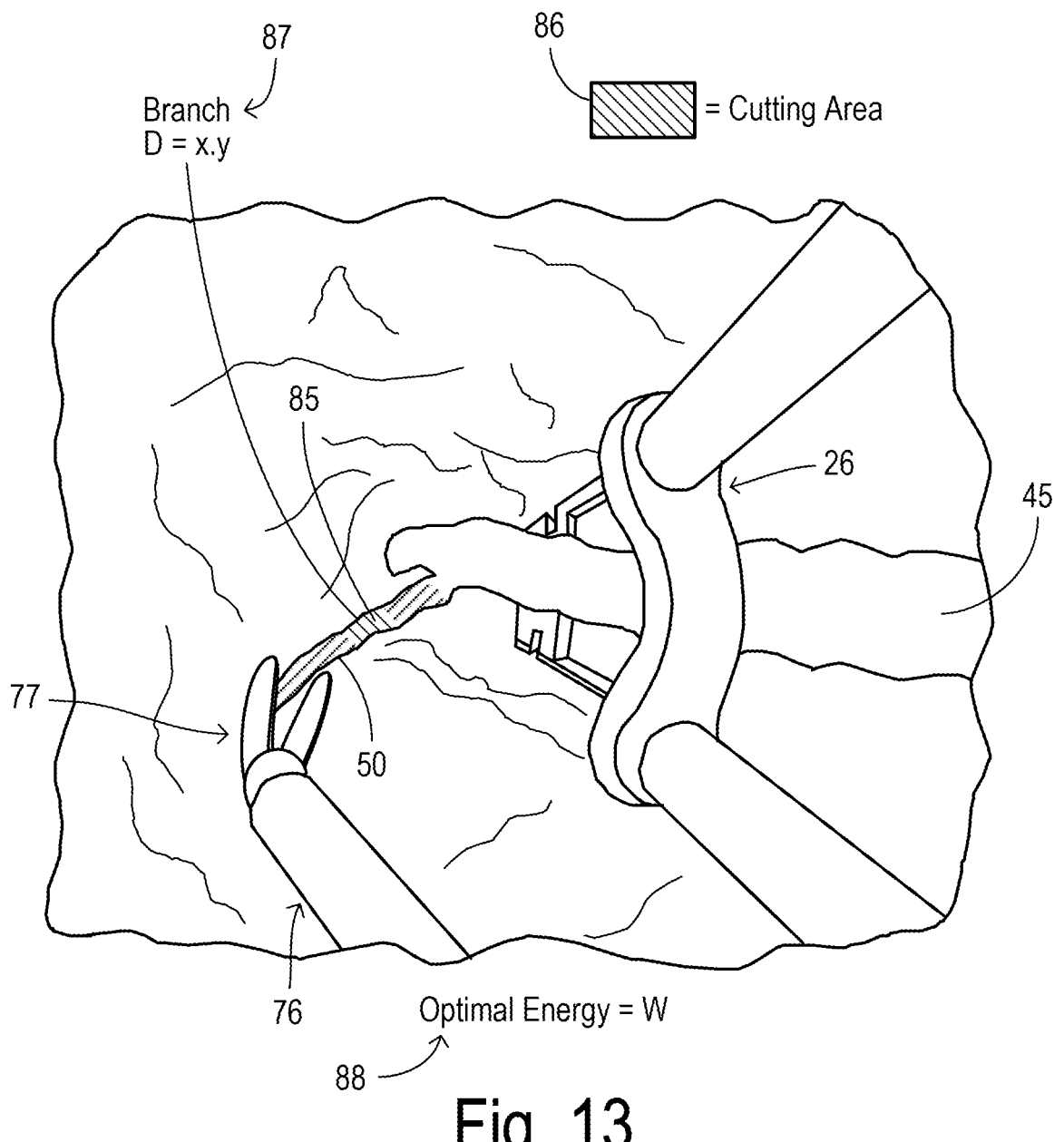
FIG. 13 shows another endoscopic visible-light view with an additional overlay superimposed on an optimal location for cutting a side branch.

In some embodiments of the disclosure, an automated analysis of images is used to identify optimal location(s) for cutting a side branch and to inform the user of the optimal location(s). For example, a diameter and length of a side branch within the tunnel can be characterized by image analysis (e.g., pattern recognition and depth detection). Dimensions of the side branch to be severed can be used to estimate an energy level (e.g., the amount of heating required) that will be sufficient to cut and cauterize it. Based on the energy level and an estimated heat flow model, a minimum required distance between the cutting location and the main target vessel can be determined. Using that minimum distance, a cutting indicator overlay 82 can be added to the viewfield as shown in FIG. 12 to provide guidance to a user. Cutting overlay 82 may including a text indicator 83 identifying the overlay as relating to a cutting zone and a pointer 84 which points out a spatial location on side branch 50 where a favorable cut can be made without expecting any great impact on the main target vessel. Overlay 82 allows temperature overlay 80 to be shown simultaneously. FIG. 13 shows an alternative embodiment wherein a Go/No-Go overlay 85 is superimposed on side branch 50 to highlight the favorable location for making a cut as well as locations where making a cut is unfavorable (e.g., because of a probability of excessive heating to the target vessel). Overlay 85 may include color tinting such as a green zone (where a cutting operation is a "Go") and a red zone (where a cutting operation is a "No Go"). A color key 86 is generated on the display in order to inform a user which tinted region corresponds to the favorable cutting area. Additionally, the image processor/controller can be equipped with a sound transducer (e.g., speaker) in order to generate audible signals which can be used for indicating a Go state or a No-Go state. For example, a warning tone may be generated when cutter 76 is located on a side branch at too close of a distance from target vessel 45.

In order to assist a user in applying an appropriate amount of heat energy sufficient for cutting/cauterizing without significant excess energy, a diameter indicator 87 may be rendered on the display according to an estimated diameter of the side branch which is calculated by the image processor/controller. The user may know from experience what amount of energy (e.g., duration of time for energizing the cutting electrodes) may be needed for side branches of various diameters. Alternatively, a recommended amount of heat energy (e.g., target energy) to be applied can be determined by the controller and displayed as an energy indicator 88. The optimal target energy for severing the side branch can be displayed as a time duration for energizing the cutter, for example. In some embodiments, the applied amount of energy may be automatically controlled once the user activates a cutting command (e.g., depresses a foot pedal or other switch) to sever the side branch.

Figure 14:
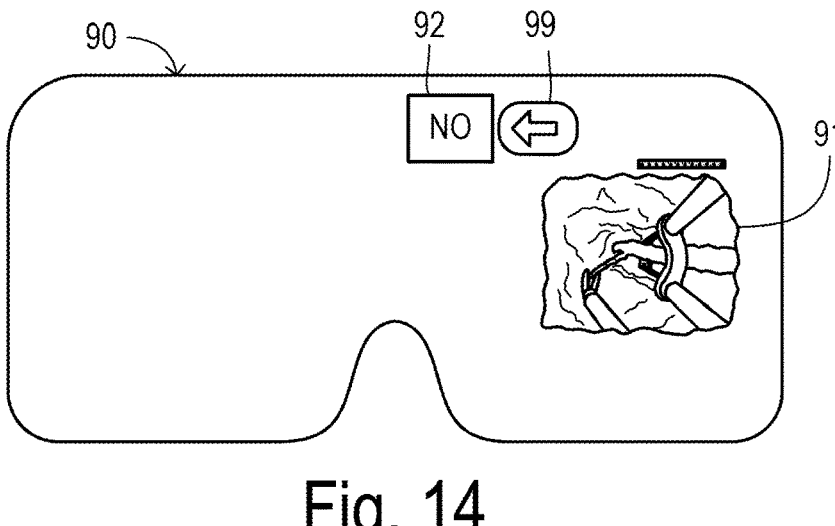
FIG. 14 is a schematic diagram showing an augmented-reality presentation with a Go/No-Go identification indicator in a "No" state and showing a cutter guidance instruction.
Figure 15:
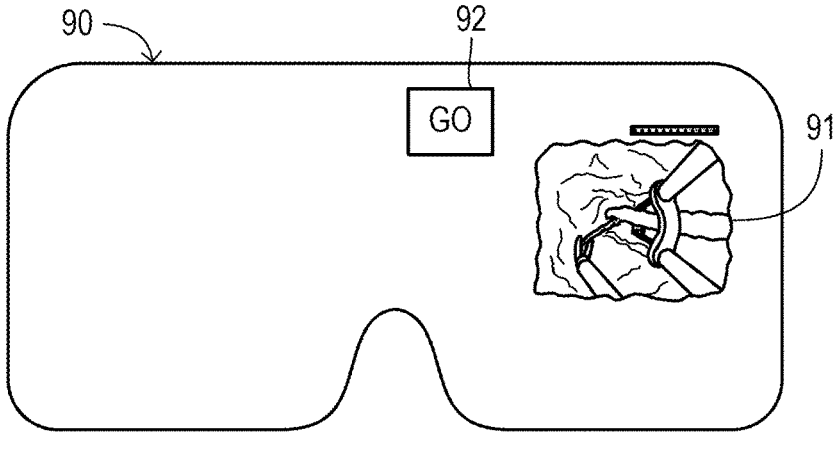
FIG. 15 is a schematic diagram showing an augmented-reality presentation with a Go/No-Go identification indicator in a "Go" state.

The camera views and overlays of FIGS. 11-13 can be displayed on a computer monitor or on an augmented-reality (AR) display. FIGS. 14 and 15 show an example of a viewfield 90 of an AR display which includes a video overlay 91 (streaming a live endoscopic view from a visible-light camera). For assisting a user to guide the cutting tool (e.g., jaws or V-cutter) to an optimal/favorable cutting location during a harvesting procedure, a flag 92 is rendered in viewfield 90 having a no-go state (FIG. 14) when the cutter is not located at the favorable location and having a go state (FIG. 15) when the cutter is located at the favorable location. When in the no-go state, viewfield 90 may include a guidance instruction overlay 99 which includes an arrow or other glyph corresponding to a direction of movement for the cutter tool jaws or V-cutter in order to achieve the favorable location. An arrow may indicate a movement to be taken within in the reference frame of the visible-light images, for example. Following the guidance instruction overlay enables the user to obtain a go state when a location is reached which keeps a heating of the target vessel below a heat threshold.

In some embodiments of the disclosure, a heat exposure to which the target vessel has been subjected is accumulated using a heat model. For example, an elevated temperature occurring at respective locations on the target vessel can be integrated over time, with the integral being rendered as a parametric display indicator. A magnitude represented on the parametric display corresponds to the accumulated heat exposure so that the user can monitor and avoid harmful exposure to the target vessel.

Figure 18:
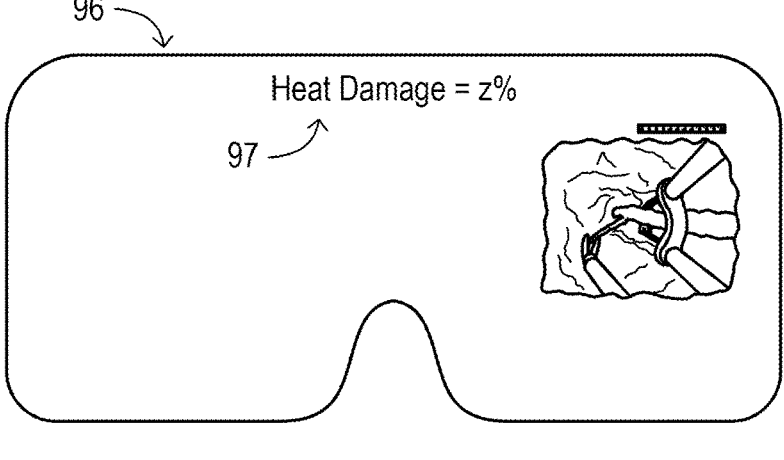
FIG. 18 is a schematic diagram showing an augmented-reality presentation including an endoscopic image and a textual overlay indicating an accumulated heat damage.
Figure 16:
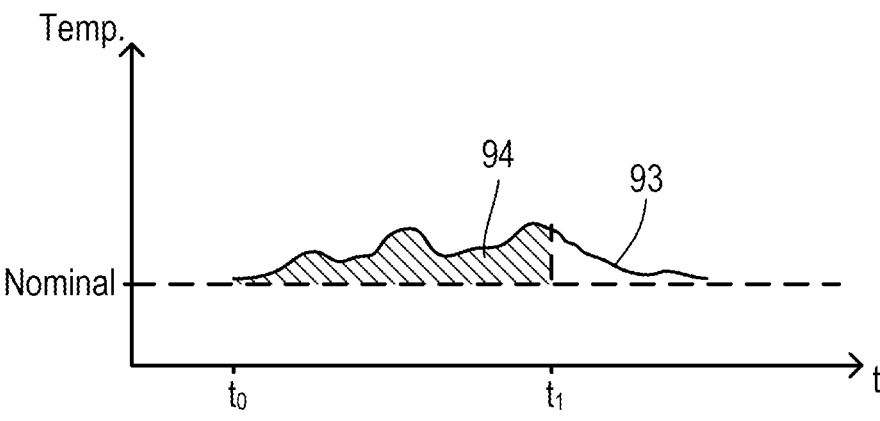
FIG. 16 is a graph showing accumulated heat energy for a particular portion of a target vessel.
Figure 17:
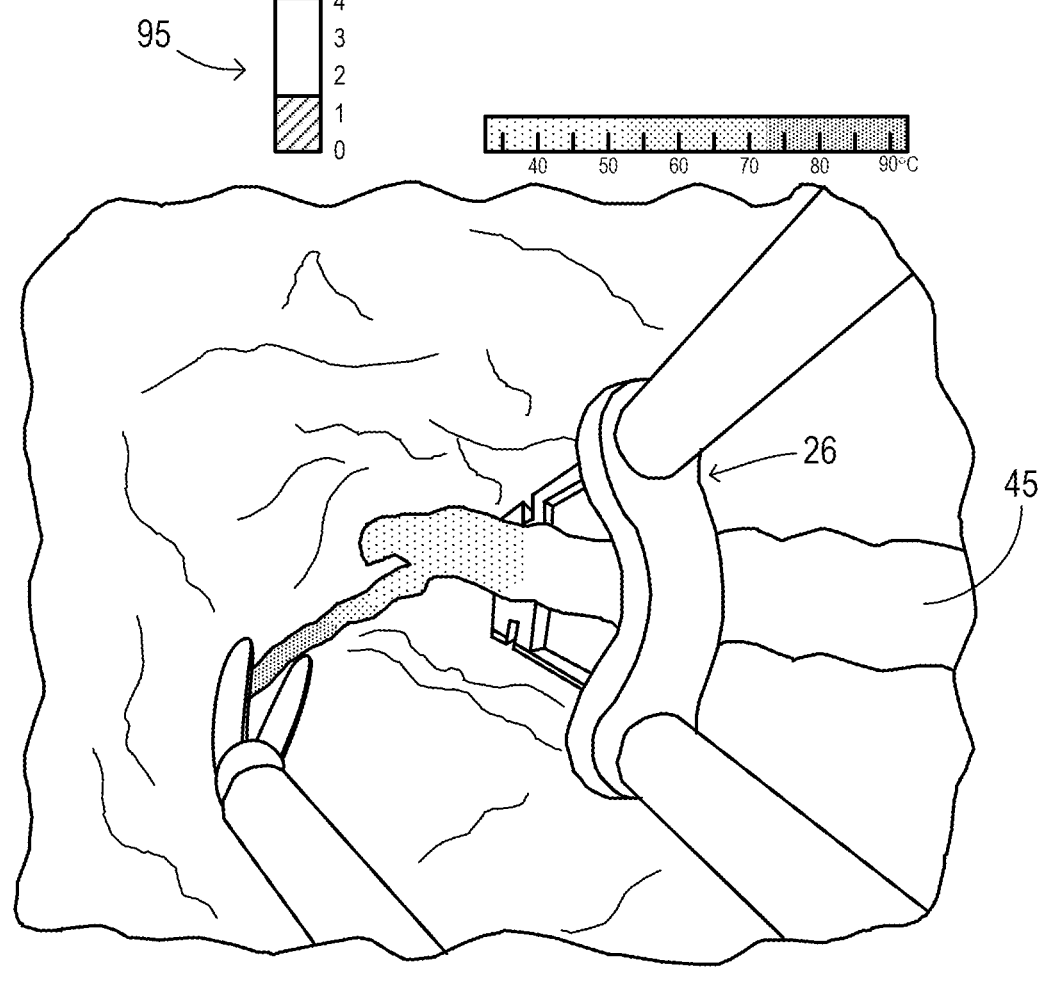
FIG. 17 is a schematic diagram showing a display of a visible-light endoscopic view and an indicator showing accumulated heat damage of a target vessel.

FIG. 16 is a graph showing a heat model wherein a trace 93 plots a measured temperature of a spot being monitored on a target vessel during a period of time. When trace 93 exceeds a nominal temperature threshold (representing a temperature at which vessel damage may begin to occur) beginning at a time $t_0$, the controller may begin to calculate an integral corresponding to an area 94 which is proportional to the excess heat energy absorbed by the target vessel. At a time $t_i$, a value of the integral proportional to area 94 can be used to determine the appearance of a parametric bar graph 95 as shown in FIG. 17 wherein a height of a colored bar indicates the integral value. An arbitrary scale may be shown in order to provide the user with a point of reference in determining the severity of the accumulated heat exposure. As shown in FIG. 18, a viewfield 96 can alternatively include a warning indicator 97 in the form of a textual message when heat damage occurs. Indicator 97 may also include data on a percentage of heat damage which may be dynamically updated as more heat accumulates in a target vessel.

Figure 19:
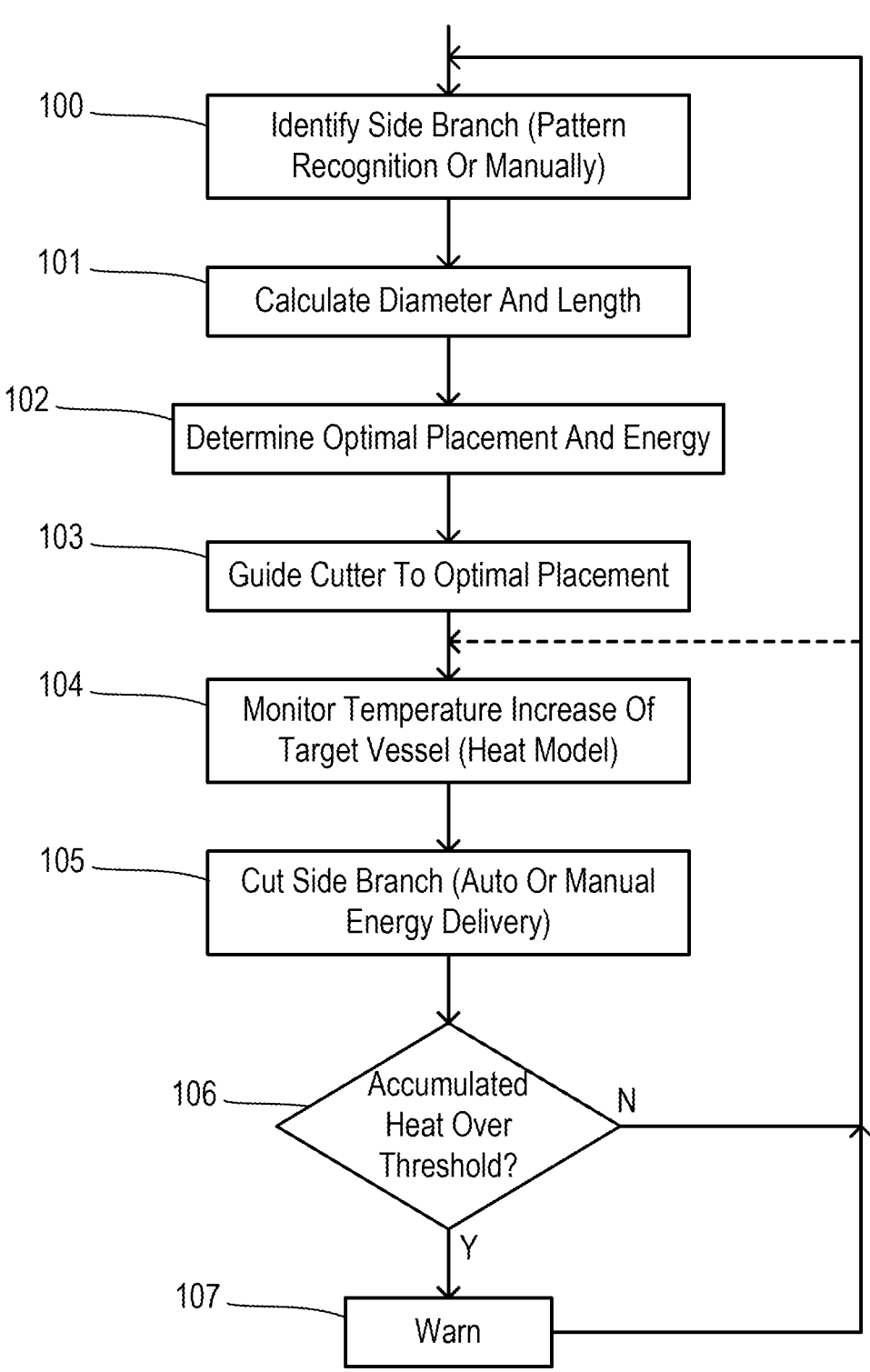
FIG. 19 is a flowchart showing a method of guiding a cutter to an optimal cutting location on a side branch and of monitoring a heat damage to a target vessel.

FIG. 19 shows a flowchart of one example method of the disclosure wherein a side branch (e.g., together with the target vessel and the branching point of the side branch) are identified in step 100. The identification can be performed automatically by pattern recognition, or could be made or assisted by a manual indication of the user. A diameter and length of a side branch are calculated in step 101. In step 102, a favorable (e.g., optimal) placement of the cutting tool and an optimal energy level are determined according to the side branch diameter and length.

In step 103, relative locations of the favorable placement and the current position of the cutting tool may be compared and guiding instructions are presented to the user (e.g., cutting indicators, markers, and movement pointers) to achieve the favorable placement. The calculated optimal energy may also be displayed to the user. When a cutting/cauterizing energy is initiated, a temperature increase of the target vessel begins to be monitored in step 104. Compression and/or thrusting of the cutting tool and delivery of thermal energy continues for the optimal time duration which may be automatically or manually controlled in step 105. In step 106, a check is performed to determine whether an accumulated heating over a nominal temperature exceeds a damage threshold. If not then a return is made to step 104 to continue monitoring or a return is made to step 100 when the current cutting operation is terminated. If the accumulated heat is above the damage threshold, then a warning is initiated in step 107.

Figure 20:
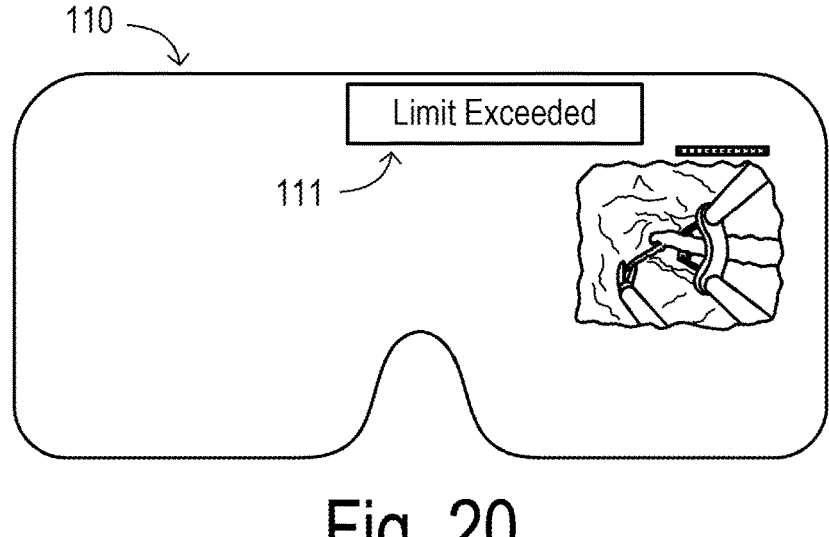
FIG. 20 depicts a schematic diagram showing an augmented-reality presentation rendering a warning message generated when accumulated heat damage exceeds a threshold.

As shown in FIG. 20, the warning may be presented on an augmented-reality display viewfield 110 as a warning indicator 111 which informs the user that the damage limit was exceeded.

What is claimed is:

1. A vessel harvesting system, the system comprising:
    an elongated harvesting instrument configured for insertion into a body along a path of a target vessel, wherein the target vessel connects to at least one side branch, and wherein the harvesting instrument includes a cutter for applying thermal energy to sever and cauterize the side branch;
    an endoscopic camera mounted to the harvesting instrument and configured for capturing visible-light images from a distal tip of the harvesting instrument within a dissected tunnel around the target vessel;
    a thermal camera mounted to the harvesting instrument and configured for capturing thermograms coinciding with the visible-light images to characterize a temperature present at respective surfaces in the dissected tunnel;
    an image processor configured for rendering a video stream including the visible-light images and an overlay configured for depicting the temperatures present on at least some of the respective surfaces when applying the thermal energy; and
    a display configured for presenting the video stream and overlay to a user,
    wherein the image processor is configured to identify the target vessel and the side branch, and wherein the image processor is configured to determine a target energy for severing the side branch according to an estimated diameter of the side branch.

2. The system of claim 1, wherein the overlay comprises a color tint including a plurality of colors corresponding to respective temperature magnitudes.

3. The system of claim 1, wherein the overlay is configured to depict the temperatures present for at least a portion of the target vessel and of the side branch.

4. The system of claim 3, wherein the image processor is configured to identify the target vessel and the side branch using image analysis.

5. The system of claim 1, wherein the image processor is configured to render a cutting indicator to guide the cutter to an optimal location for severing the identified side branch to limit a heat load applied to the target vessel.

6. The system of claim 5, wherein the cutting indicator comprises a marker pointing to a spatial location on the side branch.

7. The system of claim 5, wherein the cutting indicator comprises a highlight region superimposed on a position of the optimal location within the visible-light images.

8. The system of claim 5, wherein the cutting indicator comprises a guidance instruction corresponding to a direction of movement of the cutter to achieve the optimal location.

9. The system of claim 5, wherein the cutting indicator comprises a flag having a no-go state when the cutter is not located at the optimal location and having a go state when the cutter is located at the optimal location.

10. The system of claim 5, wherein the image processor is configured to identify the optimal location for severing the identified side branch such that a distance from the optimal location to the target vessel keeps a heating of the target vessel below a heat threshold.

11. The system of claim 1, wherein the image processor is configured to accumulate a heat exposure to which the target vessel is subjected, and wherein the image processor is configured to render a parametric display indicator corresponding to the accumulated heat exposure.

12. The system of claim 11, wherein the image processor is configured to render a warning indicator if the accumulated heat exposure is greater than a damage threshold.

13. The system of claim 1, wherein the image processor is configured to render a diameter indicator according to the estimated diameter of the side branch.

14. The system of claim 1, wherein the image processor is configured to render an energy indicator according to the target energy.

15. The system of claim 1, wherein the display comprises an augmented-reality display worn by the user.

16. A vessel harvesting system, the system comprising:

an elongated harvesting instrument configured for insertion into a body along a path of a target vessel, wherein the target vessel connects to at least one side branch, and wherein the harvesting instrument includes a cutter for applying thermal energy to sever and cauterize the side branch;

an endoscopic camera mounted to the harvesting instrument and configured for capturing visible-light images from a distal tip of the harvesting instrument within a dissected tunnel around the target vessel;

a thermal camera mounted to the harvesting instrument and configured for capturing thermograms coinciding with the visible-light images to characterize a temperature present at respective surfaces in the dissected tunnel;

an image processor configured for rendering a video stream including the visible-light images and an overlay configured for depicting the temperatures present on at least some of the respective surfaces when applying the thermal energy; and a display configured for presenting the video stream and overlay to a user, wherein the image processor is configured to identify the target vessel and the side branch, wherein the image processor is configured to render a cutting indicator to guide the cutter to an optimal location for severing the identified side branch to limit a heat load applied to the target vessel, and wherein the cutting indicator comprises a flag having a no-go state when the cutter is not located at the optimal location and having a go state when the cutter is located at the optimal location.

17. The system of claim 16, wherein the cutting indicator comprises a marker pointing to a spatial location on the side branch.

18. The system of claim 16, wherein the cutting indicator comprises a highlight region superimposed on a position of the optimal location within the visible-light images.

19. The system of claim 16, wherein the cutting indicator comprises a guidance instruction corresponding to a direction of movement of the cutter to achieve the optimal location.

20. The system of claim 16, wherein the image processor is configured to identify the optimal location for severing the identified side branch such that a distance from the optimal location to the target vessel keeps a heating of the target vessel below a heat threshold.

* * * * *